US008641638B2

(12) United States Patent
Kelleher et al.

(10) Patent No.: US 8,641,638 B2
(45) Date of Patent: *Feb. 4, 2014

(54) ELECTROMYOGRAPHY SYSTEM

(75) Inventors: Brian S. Kelleher, Ramona, CA (US);
James F. Marino, La Jolla, CA (US);
Corbett W. Stone, San Diego, CA (US);
Robin H. Vaughn, Escondido, CA (US);
Jeffrey H. Owens, Monkton, MD (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/981,889

(22) Filed: Oct. 31, 2007

(65) Prior Publication Data

US 2008/0064976 A1    Mar. 13, 2008

Related U.S. Application Data

(60) Continuation of application No. 10/830,189, filed on Apr. 21, 2004, now Pat. No. 7,963,927, which is a division of application No. 09/722,070, filed on Nov. 24, 2000, now Pat. No. 7,470,236.

(60) Provisional application No. 60/167,416, filed on Nov. 24, 1999.

(51) Int. Cl.
*A61B 5/05* (2006.01)

(52) U.S. Cl.
USPC ........................................ 600/554

(58) Field of Classification Search
USPC ............... 600/546, 554, 545, 587, 210, 373; 606/79, 170, 207, 83, 84, 90; 607/143, 607/116, 117; 340/930; 128/901, 902, 908; 604/164.11, 264, 272
See application file for complete search history.

(56) References Cited

U.S. PATENT DOCUMENTS

| | | | |
|---|---|---|---|
| 2,736,002 A | 2/1956 | Oriel | |
| 3,785,368 A | 1/1974 | McCarthy et al. | |
| 4,545,374 A * | 10/1985 | Jacobson | 600/210 |
| 4,592,369 A | 6/1986 | Davis et al. | |

(Continued)

FOREIGN PATENT DOCUMENTS

EP    0607688    7/1994

OTHER PUBLICATIONS

Neurovision SE Nerve Locator/Monitor, RLN Systems, Inc., Operators Manual, (1999), 22 pages.*

(Continued)

*Primary Examiner* — Brian Szmal
(74) *Attorney, Agent, or Firm* — Jonathan Sprangler; Rory Schermerborn

(57) ABSTRACT

Methods for determining structural integrity of a bone within the spine of a patient, the bone having a first aspect and a second aspect, wherein the second aspect separated from the first aspect by a width and located adjacent to a spinal nerve. The methods involve (a) applying an electrical stimulus to the first aspect of the bone; (b) electrically monitoring a muscle myotome associated with the spinal nerve to detect if an onset neuro-muscular response occurs in response to the application of the electrical stimulus to the first aspect of the bone; (c) automatically increasing the magnitude of the electrical stimulus to until the onset neuro-muscular response is detected; and (d) communicating to a user via at least one of visual and audible means information representing the magnitude of the electrical stimulus which caused the onset neuro-muscular response.

23 Claims, 10 Drawing Sheets

(56) References Cited

U.S. PATENT DOCUMENTS

| | | | |
|---|---|---|---|
| 4,759,377 A | | 7/1988 | Dykstra |
| 4,962,766 A | | 10/1990 | Herzon |
| 4,964,411 A | | 10/1990 | Johnson et al. |
| 5,196,015 A | | 3/1993 | Neubardt |
| 5,284,153 A | * | 2/1994 | Raymond et al. ............ 600/554 |
| 5,284,154 A | | 2/1994 | Raymond et al. |
| 5,375,067 A | | 12/1994 | Berchin |
| 5,474,558 A | * | 12/1995 | Neubardt ........................ 606/79 |
| 5,480,440 A | | 1/1996 | Kambin |
| 5,549,656 A | | 8/1996 | Reiss |
| 5,775,331 A | | 7/1998 | Raymond et al. |
| 5,779,642 A | | 7/1998 | Nightengale |
| 5,806,522 A | | 9/1998 | Katims |
| 5,928,158 A | | 7/1999 | Aristides |
| 5,935,131 A | | 8/1999 | Bonutti |
| 6,027,456 A | | 2/2000 | Feler et al. |
| 6,038,477 A | | 3/2000 | Kayyali |
| 6,104,957 A | | 8/2000 | Alo et al. |
| 6,104,960 A | | 8/2000 | Duysens et al. |
| 6,119,068 A | | 9/2000 | Kannonji |
| 6,128,576 A | | 10/2000 | Nishimoto et al. |
| 6,181,961 B1 | | 1/2001 | Prass |
| 6,266,558 B1 | | 7/2001 | Gozani et al. |
| 6,306,100 B1 | | 10/2001 | Prass |
| 6,334,068 B1 | | 12/2001 | Hacker |
| 6,466,817 B1 | | 10/2002 | Kaula et al. |
| 6,564,078 B1 | * | 5/2003 | Marino et al. ................ 600/373 |
| 6,579,244 B2 | | 6/2003 | Goodwin |
| 6,719,692 B2 | | 4/2004 | Kleffner et al. |
| 6,796,985 B2 | | 9/2004 | Bolger et al. |
| 6,819,956 B2 | | 11/2004 | DiLorenzo |
| 6,849,047 B2 | | 2/2005 | Goodwin |
| 6,855,105 B2 | | 2/2005 | Jackson, III et al. |
| 6,929,606 B2 | | 8/2005 | Ritland |
| 7,089,059 B1 | | 8/2006 | Pless |
| 2004/0225228 A1 | | 11/2004 | Ferree |
| 2005/0033380 A1 | | 2/2005 | Tanner et al. |
| 2005/0192575 A1 | | 9/2005 | Pacheco |
| 2008/0064976 A1 | | 3/2008 | Kelleher et al. |
| 2008/0064977 A1 | | 3/2008 | Kelleher et al. |

OTHER PUBLICATIONS

Calancie et al, Stimulus-Evoked EMG Monitoring During Transpedicular Lumbosacral Spine Instrumentation, Spine, 19(24), (1994), 2780-2786.*

"Brackman II EMG System", Medical Electronics, 1994, 4pages.

"Electromyography System", International Search Report, International Patent Application No. PCT/US00/32329, Apr. 27, 2001, 9 pages.

"System and Methods for Determining Nerve Proximity, Direction, and Pathology During Surgery", International Search Report, International Patent No. PCT/US02/22247, Mar. 27, 2003, 4 pages.

"Systems and Methods for Performing Percutaneous Pedicle Integrity Assessments", International Search Report, International Application No. PCT/US02/35047, Aug. 11, 2003, 5 pages.

"Systems and Methods for Performing Surgery Procedures and Assessemnts", International Search Report, International Application No. PCT/US02/30617, Jun. 5, 2003, 4 pages.

"The Brackman II EMG Monitoring System", Medical Electronics Co. Operator's Manual Version 1.1, 1995, 50 pages.

"The Nicolet Viking IV", Nicolet Biomedical Products 1999, 6 pages.

Anderson, D. G. et al., "Pedicle screws with high electrical resistance: a potential source of error with stimulus-evoked EMG", Spine. 27(14): Department of Orthopaedic Surgery, University of Virginia Jul. 15, 2002, 1577-1581.

Bose, Bikash et al., "Neurophysiologic Monitoring of Spinal Nerve Root Function During Instrumented Posterior Lumbar Spine Surgery", Spine, 27(13) 2002, 1444-1450.

Clements, David et al., "Evoked and Spontaneous Electromyography to Evaluate Lumbosacral Pedicle Screw Placement", Spine, 21(5),1996, 600-604.

Danesh-Clough, T. et al., "The use of evoked EMG in detecting misplaced thoracolumbar pedicle screws", Spine. 26(12) Orthopaedic Department, Dunedin Hospital Jun. 15, 2001, 1313-1316.

Darden, B. V. et al., "A comparison of impedance and electromyogram measurements in detecting the presence of pedicle wall breakthrough", Spine. 23(2) Charlotte Spine Center, North Carolina Jan. 15, 1998, 256-262.

Ebraheim, N. A. et al., "Anatomic relations between the lumbar pedicle and the adjacent neural structures", Spine. 22(20) Department of Orthopaedic Surgery, Medical College of Ohio, Oct. 15, 1997, 2338-2341.

Glassman, Steven et al., "A Prospective Analysis of Intraoperative Electromyographic Monitoring of Pedicle Screw Placement With Computed Tomographic Scan Confirmation", Spine , 20(12) 1995, 1375-1379.

Holland, N. R. et al., "Higher electrical stimulus intensities are required to activate chronically compressed nerve roots. Implications for intraoperative electromyographic pedicle screw testing", Spine. 23(2) Department of Neurology, Johns Hopkins University School of Medicine Jan. 15, 1998, 224-227.

Holland, Neil et al., "Intraoperative Electromyography During Thoracolumbar Spinal Surgery", Spine, 23(17) 1998, 1915-1922.

Journee, H. L. et al., "System for Intra-Operative Monitoring of the Cortical Integrity of the Pedicle During Screw Placement in Low-Back Surgery: Design and Clinical Results", Sensory and neuromuscular diagnostic instrumentation and data analysis, 18th Annual International Conference on Engineering in Medicine and Biology Society, 1(31) Oct. 1996, 144-145.

Lenke, Lawrence et al., "Triggered Electromyographic Threshold for Accuracy of Pedicle Screw Placement", Spine, 20 (14) 1995, 1585-1591.

Maguire, J. et al., "Evaluation of Intrapedicular Screw Position Using Intraoperative Evoked Electromyography", Spine, 20(9) 1995, 1068-1074.

Toleikis, J. et al., "The Usefulness of Electrical Stimulation for Assessing Pedicle Screw Replacements", Journal of Spinal Disorder, 13(4) 2000, 283-289.

Welch et al., "Evaluation with evoked and spontaneous electromyography during lumbar instrumentation : a prospective study", J. Neurosurg 87 Sep. 1997, 397-402.

* cited by examiner

ELECTROMYOGRAPHY SYSTEM

CROSS-REFERENCES TO RELATED APPLICATIONS

The present application is a continuation of commonly owned U.S. patent application Ser. No. 10/830,189 filed Apr. 21, 2004, now U.S. Pat. No. 7,963,927 which is itself a division of U.S. patent application Ser. No. 09/722,070 filed Nov. 24, 2000, now U.S. Pat. No. 7,470,236, which claims benefit under 35 U.S.C. §119(e) from U.S. Provisional Application Ser. No. 60/167,416 filed Nov. 24, 1999, the entire contents of which are all hereby expressly incorporated by reference into this disclosure as if set forth fully herein.

TECHNICAL FIELD

The present invention relates to electromyography (EMG) and to systems for detecting the presence of nerves during surgical procedures.

BACKGROUND OF THE INVENTION

It is important to avoid unintentionally contacting a patient's nerves when performing surgical procedures, especially when using surgical tools and procedures that involve cutting or boring through tissue. Moreover, it is especially important to sense the presence of spinal nerves when performing spinal surgery, since these nerves are responsible for the control of major body functions. However, avoiding inadvertent contact with these nerves is especially difficult due to the high nerve density in the region of the spine and cauda equina.

The advent of minimally invasive surgery offers great benefits to patients through reduced tissue disruption and trauma during surgical procedures. Unfortunately, a downside of such minimally invasive surgical procedures is that they tend to offer a somewhat reduced visibility of the patient's tissues during the surgery. Accordingly, the danger of inadvertently contacting and/or severing a patient's nerves can be increased.

Systems exist that provide remote optical viewing of a surgical site during minimally invasive surgical procedures. However, such systems cannot be used when initially penetrating into the tissue. Moreover, such optical viewing systems cannot reliably be used to detect the location of small diameter peripheral nerves.

Consequently, a need exists for a system that alerts an operator that a particular surgical tool, which is being minimally invasively inserted into a patient's body, is in close proximity to a nerve. As such, the operator may then redirect the path of the tool to avoid inadvertent contact with the nerve. It is especially important that such a system alerts an operator that a nerve is being approached as the surgical tool is advanced into the patient's body prior to contact with the nerve, such that a safety distance margin between the surgical tool and the nerve can be maintained.

A variety of antiquated, existing electrical systems are adapted to sense whether a surgical tool is positioned adjacent to a patient's nerve. Such systems have proven to be particularly advantageous in positioning a hypodermic needle adjacent to a nerve such that the needle can be used to deliver anesthetic to the region of the body adjacent the nerve. Such systems rely on electrifying the needle itself such that as a nerve is approached, the electrical potential of the needle will depolarize the nerve causing the muscle fibers coupled to the nerve to contract and relax, resulting in a visible muscular reaction, seen as a "twitch".

A disadvantage of such systems is that they rely on a visual indication, being seen as a "twitch" in the patient's body. During precision minimally invasive surgery, uncontrollable patient movement caused by patient twitching, is not at all desirable, since such movement may itself be injurious. In addition, such systems rely on the operator to visually detect the twitch. Accordingly, such systems are quite limited, and are not particularly well adapted for use in minimally invasive surgery.

SUMMARY OF THE INVENTION

The present invention provides methods and apparatus for informing an operator that a surgical tool or probe is approaching a nerve. In preferred aspects, the surgical tool or probe may be introduced into the patient in a minimally invasive cannulated approach. In alternate aspects, the surgical tool or probe comprises the minimally invasive cannula itself.

In a first aspect, the present invention provides a system for detecting the presence of a nerve near a surgical tool or probe, based upon the current intensity level of a stimulus pulse applied to the surgical tool or probe. When a measurable neuro-muscular (EMG) response is detected from a stimulus pulse having a current intensity level at or below a pre-determined onset level, the nerve is considered to be near the tool or probe and thus, detected.

In an optional second aspect of the invention, the onset level (i.e.: the stimulus current level at which a neuro-muscular response is detected for a particular nerve) may be based on EMG responses measured for a probe at a predetermined location relative to the nerve. Specifically, onset levels may first be measured for each of a plurality of spinal nerves, (yielding an initial "baseline" set of neuro-muscular response onset threshold levels), which are then used in the first (nerve detection) aspect of the invention. Therefore, in accordance with this optional second aspect of the invention, a system for determining relative neuro-muscular onset values (i.e.: EMG response thresholds), for a plurality of spinal nerves is also provided. Accordingly, the pre-determined onset level may be compared to the current level required to generate a measurable EMG response for a tool or probe being advanced toward one or more nerves of interest.

In alternate aspects, however, the neuro-muscular onset values that are used to accomplish the first (nerve detection) aspect of the invention are not measured for each of the patient's plurality of spinal nerves. Rather, pre-determined levels of current intensity (below which neuro-muscular responses are detected in accordance with the first aspect of the invention) can instead be directly pre-set into the system. Such levels preferably correspond to specific expected or desired onset threshold values, which may have been determined beforehand by experimentation on other patients.

In the aspect of the invention where initial "baseline" neuro-muscular onset values are determined prior to nerve detection, such onset values can optionally be used to calibrate the present nerve-detection system (which in turn operates to detect whether an minimally invasive surgical tool or probe is positioned adjacent to a spinal nerve).

It is to be understood, therefore, that the present invention is not limited to systems that first determine relative neuro-muscular onset values, and then use these neuro-muscular onset values to detect the presence of a nerve. Rather, the present invention includes an optional system to first determine relative neuro-muscular onset values and a system to detect the presence of a nerve (using the neuro-muscular onset values which have been previously determined). As such, the present invention encompasses systems that also use fixed neuro-muscular onset values (which may simply be input into the system hardware/software by the operator prior to use) when performing electromyographic monitoring of spinal nerves to detect the presence of a spinal nerve adjacent a tool or probe.

In optional aspects, the preferred method of sensing for the presence of a nerve may be continuously repeated as the probe/surgical tool is physically advanced further into the patient such that the operator is warned quickly when the probe/surgical tool is closely approaching the nerve.

In the first (nerve sensing) aspect of the invention, the present nerve-detection system comprises an electrode or electrodes positioned on the distal end of the surgical tool or probe, with an electromyographic system used to detect whether a spinal nerve is positioned adjacent to the surgical tool or probe. A conclusion is made that the surgical tool or probe is positioned adjacent to a spinal nerve when a neuro-muscular (e.g.: EMG) response to a stimulus pulse emitted by the electrode or electrodes on the surgical tool or probe is detected (at a distant myotome location, such as on the patient's legs) at or below certain neuro-muscular response onset values (i.e.: pre-determined current intensity levels) for each of the plurality of spinal nerves. The stimulus pulse itself may be emitted from a single probe, but in an optional aspect, the stimulus pulse may be emitted from separate left and right probes with the signals being multiplexed. As stated above, such pre-determined levels may be pre-input by the operator (or be pre-set into the system's hardware or software) and may thus optionally correspond to known or expected values. (For example, values as measured by experimentation on other patients).

In accordance with the optional second (neuro-muscular response onset value determination) aspect of the invention, the neuro-muscular response onset values used in nerve detection may instead be measured for the particular patient's various nerves, as follows.

Prior to attempting to detect the presence of a nerve, an EMG stimulus pulse is first used to depolarize a portion of the patient's cauda equina. This stimulus pulse may be carried out with a pulse passing between an epidural stimulating electrode and a corresponding skin surface return electrode, or alternatively, between a pair of electrodes disposed adjacent to the patient's spine, or alternatively, or alternatively, by a non-invasive magnetic stimulation means. It is to be understood that any suitable means for stimulating (and depolarizing a portion of) the patient's cauda equina can be used in this regard.

After the stimulus pulse depolarizes a portion of the patient's cauda equina, neuro-muscular (i.e., EMG) responses to the stimulus pulse are then detected at various myotome locations corresponding to a plurality of spinal nerves, with the current intensity level of the stimulus pulse at which each neuro-muscular response is first detected being the neuro-muscular response "onset values" for each of the plurality of spinal nerves.

It is to be understood that the term "onset" as used herein is not limited to a condition in which all of the muscle fibers in a bundle of muscle fibers associated with a particular nerve exhibit a neuro-muscular response. Rather, an "onset" condition may comprise any pre-defined majority of the muscle fibers associated with a particular nerve exhibit a neuro-muscular response.

In an additional aspect of the invention, the relative neuro-muscular response onset values can be repeatedly re-determined (at automatic intervals or at intervals determined by the operator) so as to account for any changes to the response onset values caused by the surgical procedure itself. Accordingly, a further advantage of the present invention is that it permits automatic re-assessment of the nerve status, with the relative neuro-muscular response onset values for each of the plurality of spinal nerves being re-determined before, during and after the surgical procedure, or repeatedly determined again and again during the surgical procedure. This optional aspect is advantageous during spinal surgery as the surgery itself may change the relative neuro-muscular response onset values for each of the plurality of nerves, such as would be caused by reducing the pressure on an exiting spinal nerve positioned between two adjacent vertebrae. This periodic re-determination of the onset values can be carried out concurrently with the nerve sensing function.

Accordingly, an advantageous feature of the present invention is that it can simultaneously indicate to an operator both: (1) nerve detection (i.e.: whether the surgical tool/probe is near a nerve); and (2) nerve status changes (i.e.: the change in each nerve's neuro-muscular response onset values over time). The surgeon is thus able to better interpret the accuracy of nerve detection warnings by simultaneously viewing changes in the various onset levels. For example, should the surgeon note that a particular onset value (i.e.: the current level of a stimulus pulse required to elicit an EMG response for a particular nerve) is increasing, this would tend to show that this nerve pathway is becoming less sensitive. Accordingly, a "low" warning may be interpreted to more accurately correspond to a "medium" likelihood of nerve contact; or a "medium" warning may be interpreted to more accurately correspond to a "high" likelihood of nerve contact.

Optionally, such re-assessment of the nerve status can be used to automatically re-calibrate the present nerve detection system. This can be accomplished by continually updating the onset values that are then used in the nerve detection function.

In preferred aspects, the neuro-muscular response onset values for each of the plurality of spinal nerves are measured at each of the spaced-apart myotome locations, and are visually indicated to an operator (for example, by way of an LED scale). Most preferably, the measuring of each of the various neuro-muscular response onset values is repeatedly carried out with the present and previously measured onset value levels being simultaneously visually indicated to an operator such as by way of the LED scale.

Accordingly, in one preferred aspect, for example, different LED lights can be used to indicate whether the value of each of the various neuro-muscular response onset values is remaining constant over time, increasing or decreasing. An advantage of this optional feature of the invention is that a surgeon operating the device can be quickly alerted to the fact that a neuro-muscular response onset value of one or more of the spinal nerves has changed. Should the onset value decrease for a particular nerve, this may indicate that the nerve was previously compressed or impaired, but become uncompressed or no longer impaired.

In a particular preferred embodiment, example, a blue LED can be emitted at a baseline value (i.e.: when the neuro-muscular response onset value remains the same as previously measured); and a yellow light can be emitted when the neuro-muscular response onset value has increased from that previously measured; and a green light being emitted when the neuro-muscular response onset value has decreased from that previously measured.

In an alternate design, different colors of lights may be simultaneously displayed to indicate currently measured onset values for each of the plurality of spinal nerve myotome locations, as compared to previously measured onset values. For example, the present measured onset value levels for each of the plurality of spinal nerve myotome locations can appear as yellow LED lights on the LED scale, with the immediately previously measured onset value levels simultaneously appearing as green LED lights on the LED scale. This also allows the operator to compare presently measured (i.e. just updated) neuro-muscular response onset values to the previously measured neuro-muscular response onset values.

In preferred aspects, the present system also audibly alerts the operator to the presence of a nerve. In addition, the volume or frequency of the alarm may change as the probe/tool moves closer to the nerve.

In a preferred aspect of the present invention, the neuro-muscular onset values, (which may be detected both when initially determining the relative neuro-muscular response onset values in accordance with the second aspect of the invention, and also when detecting a neuro-muscular onset response to the emitted stimulus pulse from the probe/tool in accordance with the first aspect of the invention), are detected by monitoring a plurality of distally spaced-apart myotome locations which anatomically correspond to each of the spinal nerves. Most preferably, these myotome locations are selected to correspond to the associated spinal nerves that are near the surgical site. Therefore, these myotome locations preferably correspond with distally spaced-apart on the patient's legs (when the operating site is in the lower vertebral range), but may also include myotome locations on the patient's arms (when the operating site is in the upper vertebral range). It is to be understood, however, that the present system therefore encompasses monitoring of any relevant myotome locations that are innervated by nerves in the area of surgery. Therefore, the present invention can be adapted for use in cervical, thoracic or lumbar spine applications.

During both the optional initial determination of the relative neuro-muscular response onset values for each of the plurality of spinal nerves (i.e.: the second aspect of the invention) and also during the detection of neuro-muscular onset responses to the stimulus pulse from the surgical probe/tool (i.e.: the first aspect of the invention), the emission of the stimulus pulse is preferably of a varying current intensity. Most preferably, the stimulus pulse is incrementally increased step-by-step in a "staircase" fashion over time, at least until a neuro-muscular response signal is detected. The stimulus pulse itself may be delivered either between a midline epidural electrode and a return electrode, or between two electrodes disposed adjacent the patient's spine, or from an electrode disposed directly on the probe/tool, or by other means.

An important advantage of the present system of increasing the level of stimulus pulse to a level at which a response is first detected is that it avoids overstimulating a nerve (which may cause a patient to "twitch"), or cause other potential nerve damage.

In optional preferred aspects, the "steps" of the staircase of increasing current intensity of the stimulus pulse are carried out in rapid succession, most preferably within the refractory period of the spinal nerves. An advantage of rapidly delivering the stimulus pulses within the refractory period of the spinal nerves is that, at most, only a single "twitch" will be exhibited by the patient, as opposed to a muscular "twitching" response to each level of the stimulation pulse as would be the case if the increasing levels of stimulus pulse were instead delivered at intervals of time greater than the refractory period of the nerves.

In another optional preferred aspect, a second probe is added to the present system, functioning as a "confirmation electrode". In this optional aspect, an electrode or electroded surface on the second probe is also used to detect the presence of a nerve, (using the same system as was used for the first probe to detect a nerve). Such a second "confirmation electrode" probe is especially useful when the first probe is an electrified cannula itself, and the second "confirmation electrode" probe is a separate probe that can be advanced through the electrified cannula. For example, as the operating (electrified) cannula is advanced into the patient, this operating cannula itself functions as a nerve detection probe. As such, the operating cannula can be advanced to the operating site without causing any nerve damage. After this cannula has been positioned at the surgical site, it may then be used as the operating cannula through which various surgical tools are then advanced. At this stage, its nerve-sensing feature may be optionally disabled, should this feature interfere with other surgical tools or procedures. Thereafter, (and at periodic intervals, if desired) the second "confirmation electrode" probe can be re-advanced through the operating cannula to confirm that a nerve has not slipped into the operating space during the surgical procedure. In the intervals of time during which this second "confirmation electrode" probe is removed from the operating cannula, access is permitted for other surgical tools and procedures. The second "confirmation electrode" probe of the present invention preferably comprises a probe having an electrode on its distal end. This confirmation electrode may either be mono-polar or bi-polar.

In an optional preferred aspect, the second "confirmation electrode" probe may also be used as a "screw test" probe. Specifically, the electrode on the secondary "confirmation" probe may be placed in contact with a pedicle screw, thereby electrifying the pedicle screw. Should the present invention detect a nerve adjacent such an electrified pedicle screw, this would indicate that pedicle wall is cracked (since the electrical stimulus pulse has passed out through the crack in the pedicle wall and stimulated a nerve adjacent the pedicle).

An advantage of the present system is that it may provide both nerve "detection" (i.e.: sensing for the presence of nerves as the probe/tool is being advanced) and nerve "surveillance" (i.e.: sensing for the presence of nerves when the probe/tool had been positioned).

A further important advantage of the present invention is that it simultaneously monitors neuro-muscular responses in a plurality of different nerves. This is especially advantageous when operating in the region of the spinal cord due to the high concentration of different nerves in this region of the body. Moreover, by simultaneously monitoring a plurality of different nerves, the present system can be used to indicate when relative nerve response onset values have changed among the various nerves. This information can be especially important when the surgical procedure being performed can alter the relative nerve response onset value of one or more nerves with respect to one another.

A further advantage of the present system is that a weaker current intensity can be applied at the nerve detecting electrodes (on the probe) than at the stimulus (i.e.: nerve status) electrodes.

DESCRIPTION OF THE PREFERRED EMBODIMENT

The present invention sets forth systems for detecting when a nerve is near or adjacent to an electrified surgical tool, probe, cannula, or other surgical instrument. The present invention also involves optional systems for simultaneously determining the "status" (e.g.: sensitivity) of a plurality of nerves.

As will be explained, the present system involves applying a signal with a current level to a probe near a nerve and determining whether an electromyographic "EMG" (i.e.: neuro-muscular) response for a muscle coupled to the nerve is present.

In preferred aspects, the present system applies a signal with a known current level (mA) to a "probe" (which could be midline probe, a cannula, a needle, etc.) Depending on the current level, distance to the nerve, and health of the nerve, an EMG may be detected in a muscle coupled to the nerve. In accordance with preferred aspects, an EMG response is determined to have been detected when the peak-to-peak response of the EMG signal is greater than some level (mVolts). In other words, an EMG response is determined to have been detected when the stimulus current level generates an EMG having a peak-to-peak value greater than a pre-determined level (for example, 60 mV or 80 mV in spinal nerve applications.) Such stimulus current level at which an EMG response is detected is termed the "onset" current level for the nerve.

In optional aspects, the present invention also sets forth systems for determining these onset current values (i.e.: determining the stimulus current level at which an EMG response is detected with a maximum peak-to-peak value greater than a predetermined level). Such onset values may be determined for a plurality of nerves either in absolute terms, or in relation to one another.

The first aspect of the present invention involves nerve detection. In the optional second aspect of the invention, nerve status information may be used to aid nerve detection. The nerve status aspect determines the minimum current level of a signal applied to a probe near a nerve needed to generate onset EMG response for a muscle coupled to a nerve of interest. The present invention may use this determined minimum current level when determining whether a probe is near the same nerve.

In optional aspects, the present invention may involve determining an initial set of "baseline" neuro-muscular response onset values for a plurality of different spinal nerve pathways. This optional second (nerve status) aspect of the present invention is preferably carried out prior to the first (nerve detection) aspect of the invention, with the initial set of "baseline" neuro-muscular onset values then optionally being used in the nerve detection function, as will be explained below. As the optional second aspect of the invention is carried out prior to carrying out the first aspect of the invention, it will be described first.

Figure 1:
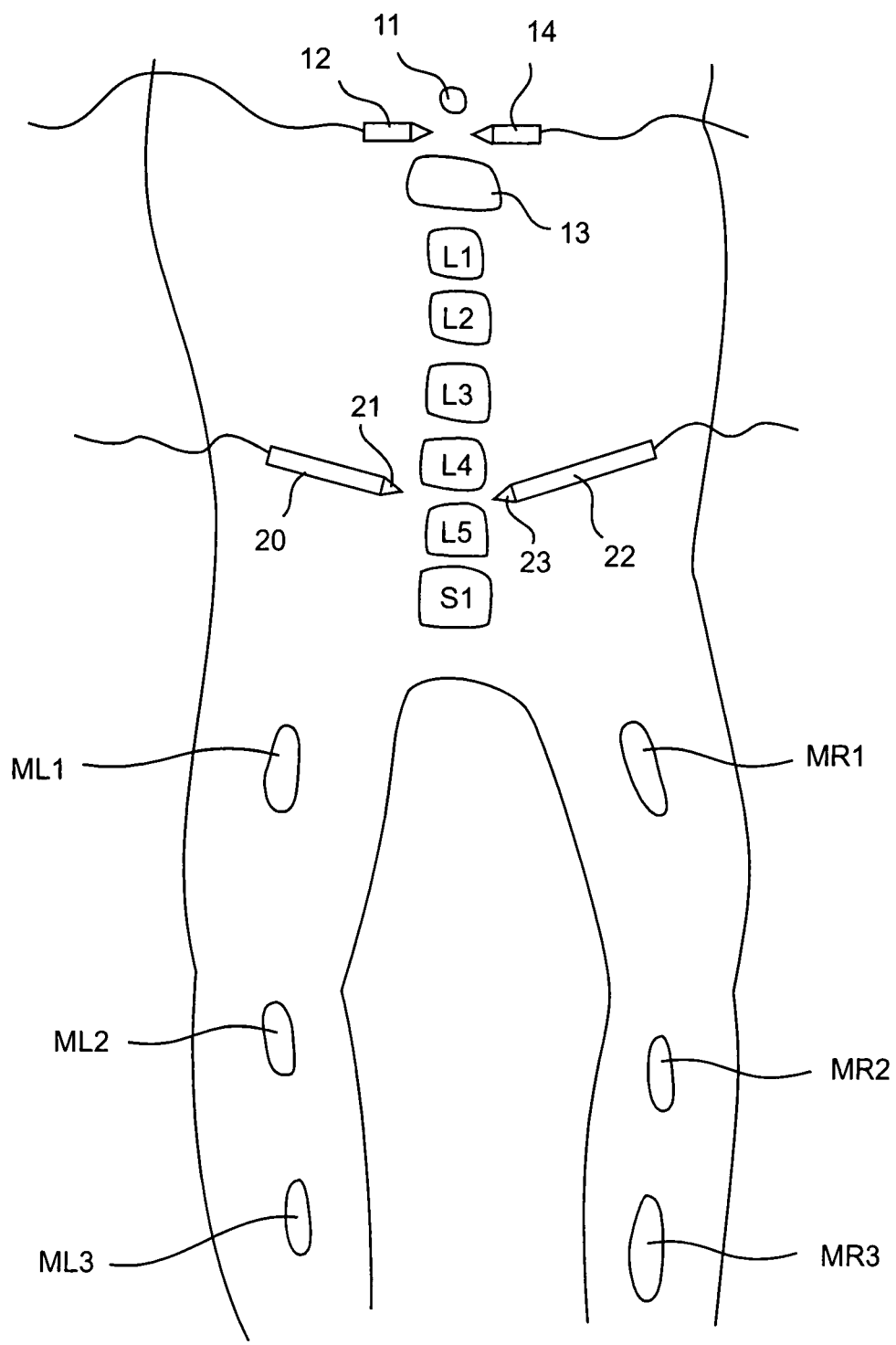
FIG. 1 is an illustration of various components of the present invention in operation.

In the nerve status determination, the minimum current level of a signal applied to a probe needed to generate an onset neuro-muscular response (i.e.: EMG response) is first determined for each of a plurality of nerves, as follows. Referring to FIG. 1, a patient's vertebrae L1, L2, L3, L4, L5, and S1 are shown. In a preferred aspect of the present invention, a portion of the patient's cauda equina is stimulated (i.e. depolarized). This depolarization of a portion of the patient's cauda equina may be achieved by conducting a stimulus pulse having a known current level between an epidural stimulating electrode 11 and a patient return electrode 13. Electrodes 11 and 13 are referred to herein as "status" electrodes, as they assist in determining the initial status of the various nerve pathways). The epidural electrode is placed in the epidural space of the spine. Alternatively, the depolarization of a portion of the patient's cauda equina may be achieved by conducting a stimulus pulse having a known current level between a pair of status (baseline) electrodes 12 and 14, which may be positioned adjacent the (thoracic/lumbar) T/L junction (above vertebra L1), as shown. Status electrodes 12 and 14 may be positioned in-line at the T/L junction, (as shown in FIG. 1). Status electrodes 12 and 14 could also be positioned on opposite lateral sides of the T/L junction.

In a preferred aspect, neuro-muscular (i.e., EMG), responses to the stimulus pulse by muscles coupled to nerves near the stimulating electrode are detected by electrodes positioned at each of a plurality of myotome locations MR1, MR2, and MR3 on the patient's right leg, and myotome locations ML1, ML2, and ML3 on the patient's left leg. The sensing of neuro-muscular responses at these locations may be performed with needle electrodes, or electrodes placed on the surface of the patient's skin, as desired. An EMG response at each location MR1 to MR6 is detected when the maximum peak-to-peak height of the EMG response to the stimulus pulse is greater than a predetermined mV value (called "onset"). Accordingly, the current level required to elicit an onset EMG response is called the "onset" current level. As described below, the current level of the stimulus pulse or signal applied to the electrode 11 or electrodes 12, 14 may be incremented from a low level until an onset EMG response is detected for one or more of the myotome locations MR1 to ML3.

It is to be understood that myotome sensing may be carried out at more than the three distal locations illustrated on each of the patient's legs in FIG. 1. Generally, as greater numbers of distal myotome locations are monitored, a greater number of spinal nerves corresponding to each of these myotome locations can be individually monitored, thereby enhancing the present system's nerve detection ability over a larger section of the patient's spinal column.

It is also to be understood that the present invention can be easily adapted to cervical or thoracic spinal applications (in addition to the illustrated lumbar application of FIG. 1). In this case an appropriate portion of the spinal column is depolarized and myotome-sensing locations are selected according to the physiology of the associated nerves for portion of the spinal column of interest. In exemplary aspects, therefore, preferred myotome-sensing locations may therefore include locations on the patient's arms, anal sphincter, bladder, and other areas, depending upon the vertebrae level where the spinal surgery is to be performed.

Figure 2:
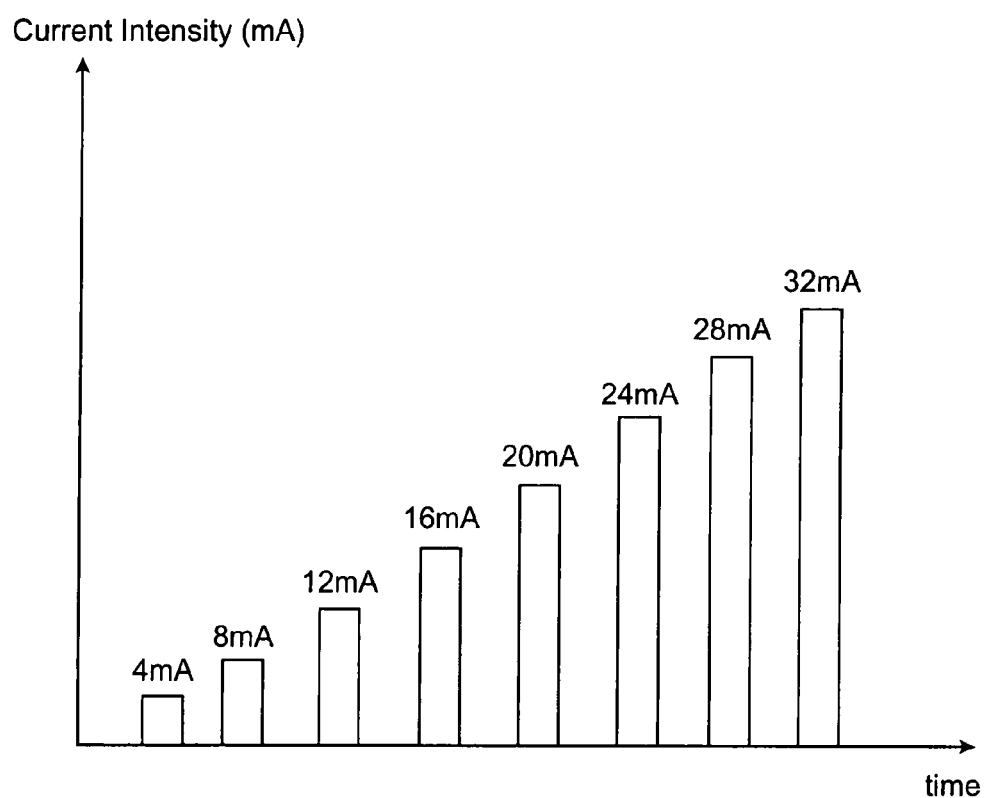
FIG. 2 shows a current intensity staircase for an electromyographic stimulation (nerve status) electrode.

In a preferred aspect, the current level of the stimulus signal conducted between status electrodes 11 and 13 (or 12 and 14) is incrementally increased in a staircase fashion as shown in the current staircase of FIG. 2 from a low value until an onset EMG response is detected at one or more myotome locations. In a preferred embodiment, onset EMG response peak-to-peak value is between 60 mV and 80 mV. (It is noted, however, that depending on the location the stimulating electrode relative to the nerve corresponding to a myotome and the nerve health/status, an onset EMG response may not be detected as the current level is incremented from the lowest level to the highest level shown in FIG. 2.) In the illustrated exemplary aspect, the current level is shown as increasing from 4 mA to 32 mA, in eight 4 mA increments where the current level is incremented until an onset EMG response is detected. The present invention is not limited to these values and other current ranges (and other numbers "steps" in the staircase) may also be used, as is desired.

At lower current levels, an onset neuro-muscular (i.e., EMG) responses to the stimulus pulse may not be detected at each myotome ML1 to MR3 location. However, as the current level of the stimulus signal is incrementally increased (i.e.: moving up the staircase, step-by-step), an onset neuro-muscular (i.e., EMG) response may eventually be detected at each of the various myotome locations ML1 through MR3 for each of the six associated spinal nerves. As noted whether an onset EMG response is detected for myotome depends on the location of the electrode relative to the corresponding nerve and the nerve status/health. For example, when a nerve is compressed or impaired, the current level required to generate an onset EMG response may be greater than the similar, non-compressed nerve at a similar distance from the stimulating electrode. Accordingly, the onset neuro-muscular response for each of the various myotome ML1 to MR3 locations may be elicited at different stimulus current levels due at least in part to the various individual spinal nerves being compressed, impaired, etc., and also due simply to differences in the individual nerve pathway sensitivities.

For example, referring to the example illustrated in FIG. 1, a stimulus signal having an initial current level is conducted between electrodes 11 and 13 (or between electrodes 12 and 14). The current level of the stimulus pulse is increased step-by-step according to the intensity staircase shown in FIG. 2 until an onset EMG response is detected at one or more selected myotomes. In particular, a response to the increasing current level stimulus pulse is detected at each of the various myotome locations ML1 through MR3. Because each of the spinal nerve paths corresponding to the various myotome locations ML1 through MR3 may have different sensitivities (as noted), different onset EMG responses may be detected at the different onset current levels for different myotome locations.

For example, Table 1 illustrates the current level required to elicit an onset EMG response for myotome location. As seen in Table 1, myotome location ML1 detected an onset EMG response to the stimulus pulse for a current level of 4 mA. Similarly, myotome MR2 detected an onset neuro-muscular/EMG response to the stimulus pulse for a current level of 24 mA, etc. Summarizing in tabular form:

TABLE 1

Stimulus Current Level at Which Onset EMG Response is Detected:

| ML1 - 4 mA | MR1 - 16 mA |
|---|---|
| ML2 - 16 mA | MR2 - 24 mA |
| ML3 - 20 mA | MR3 - 12 mA |

The above detected stimulus current levels may then be optionally scaled to correspond to stimulus staircase levels 1 through 8, with the maximum signal strength of 32 mA corresponding to "8", as follows, and as illustrated for each of Myotome locations ML1 to MR3, as shown in Table 2 based on the levels shown in Table 1.

TABLE 2

Scaled Neuro-muscular Response Onset Values:

| ML1 - 1 | MR1 - 4 |
|---|---|
| ML2 - 4 | MR2 - 6 |
| ML3 - 5 | MR3 - 3 |

Accordingly, by depolarizing a portion of the patient's cauda equina and by then measuring the current amplitude at which an onset neuro-muscular (i.e., EMG) response to the depolarization of the cauda equina is detected in each of a plurality of spinal nerves, (i.e.: at each of the myotome locations corresponding to each of the individual spinal nerves), a method for determining the relative neuro-muscular response for each of the plurality of spinal nerves is provided. As such, the relative sensitivities of the various spinal nerve pathways with respect to one another can initially be determined. This information may represent the relative health or status of the nerves coupled to each myotome location where the stimulating electrode is approximately the same distance from each of the corresponding nerves. For example, the nerve corresponding to myotome location MR2 required 24 mA to elicit an onset EMG response in the corresponding muscle. Accordingly, this nerve may be compressed or otherwise physiologically inhibited.

These respective stimulus pulse current levels at which an onset neuro-muscular response is detected for each of myotome locations ML1 through MR3 are detected may then be electronically stored (as an initial "baseline" set of onset EMG response current levels). In a preferred aspect, these stored levels may then be used to perform nerve detection for a probe at a location other than the midline as will be explained. As noted, once an onset neuro-muscular or EMG-response has been detected for each of the myotome locations, it is not necessary to apply further increased current level signals. As such, it may not be necessary for the current level of the signal to reach the top of the current level staircase (as shown in FIG. 2) (provided a response has been detected at each of the myotome locations).

Figure 8A:
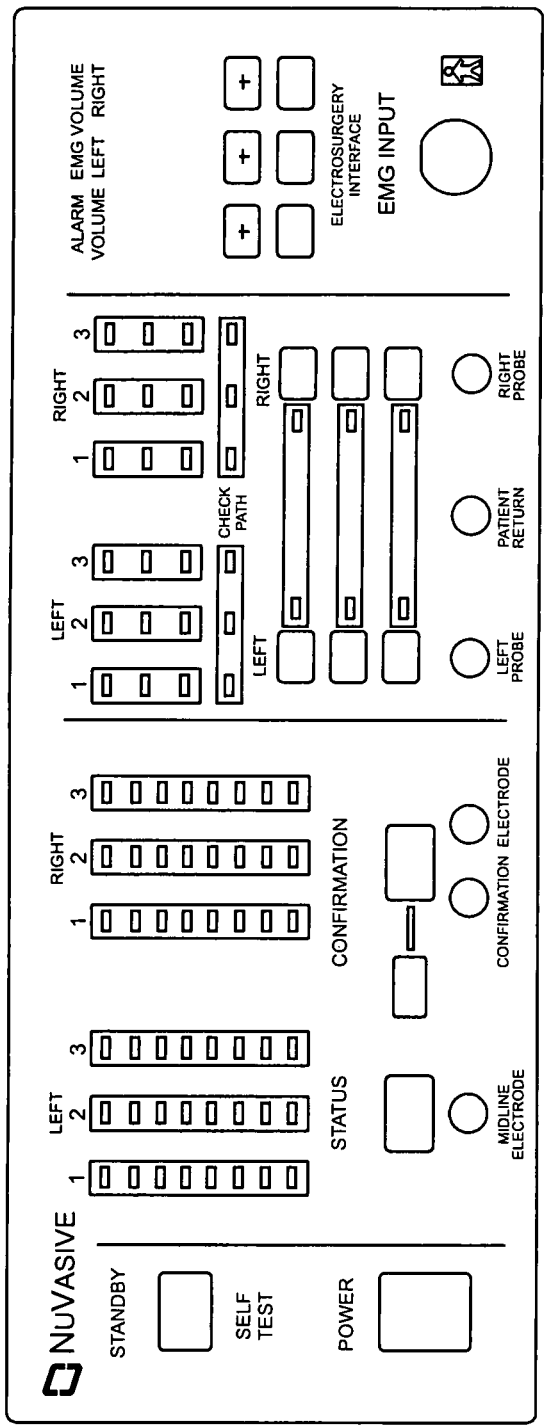
FIG. 8A is an illustration of the front panel of one design of the present nerve status and detection system.
Figure 8B:
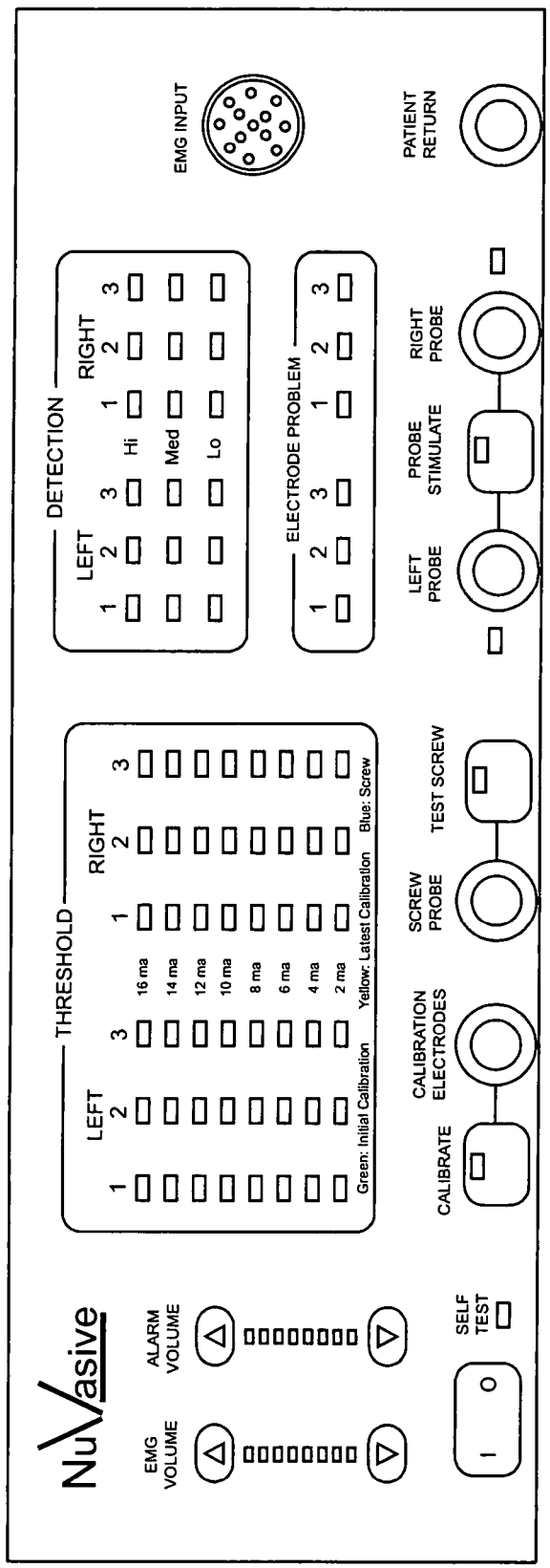
FIG. 8B is an illustration of the front panel of another design of the present nerve status and detection system.
Figure 9:
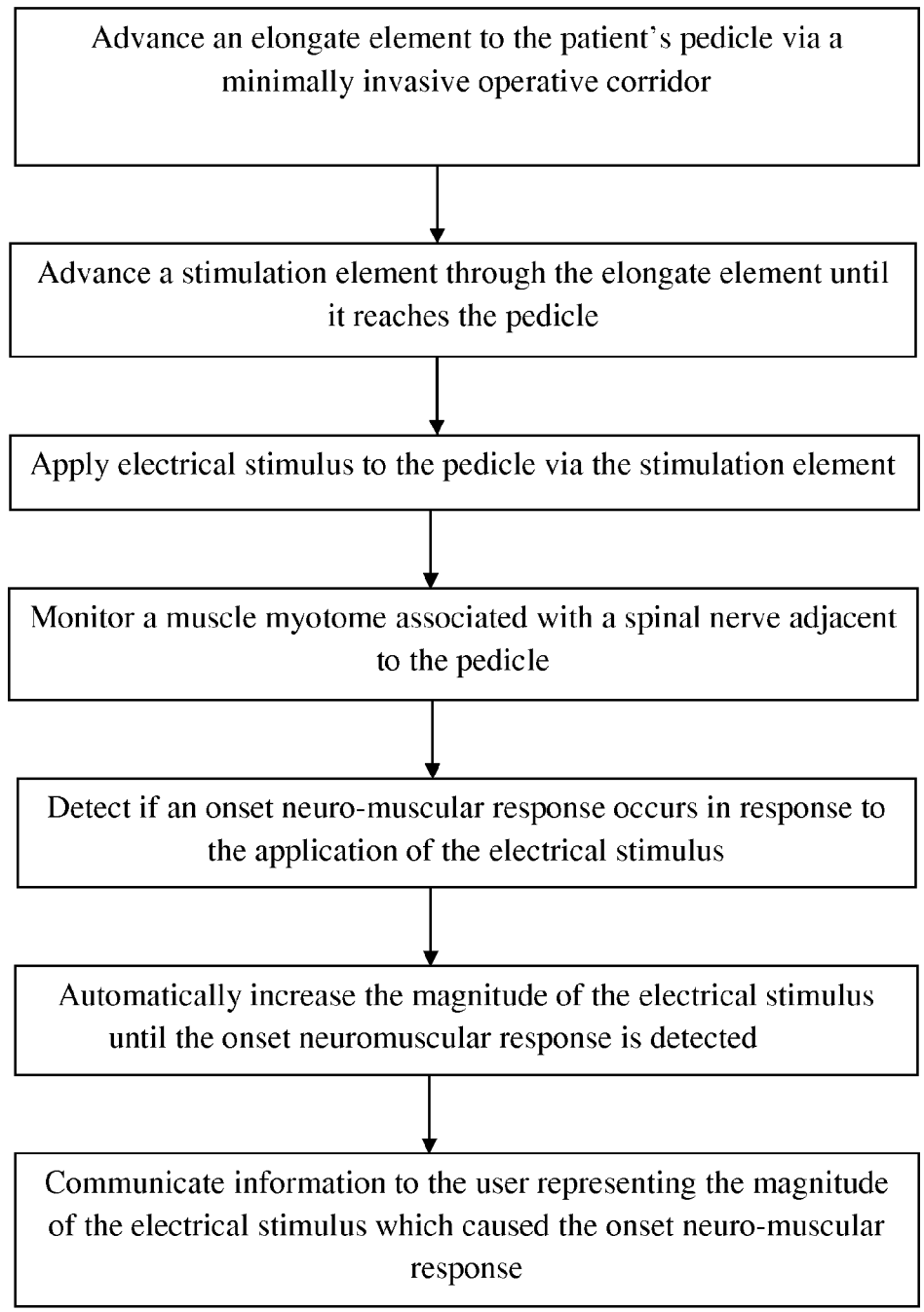
FIG. 9 is a flow chart illustrating an example method for testing the integrity of a pedicle via a minimally invasive approach.

By either reaching the end of the increasing current amplitude staircase, (or by simply proceeding as far up the staircase as is necessary to detect a response at each myotome location), the present system obtains and stores an initial "baseline" set of current level onset values for each myotome location. These onset values may be stored either as absolute (i.e.: mA) or scaled (i.e.: 1 to 8) values. As noted these values represent the baseline or initial nerve status for each nerve corresponding to one of the myotome locations. This baseline onset current level may be displayed as a fixed value on a bar graft of LEDs such as shown in FIGS. 8A or 8B. At a later point, the nerve status of the nerves corresponding to the myotomes may be determined again by applying a varying current level signal to the midline electrodes. If a procedure is being performed on the patient, the onset current level for one or more of the corresponding nerves may change.

When the onset current level increases for a nerve this may indicate that a nerve has been impacted by the procedure. The increased onset current level may also be displayed on the bar graft for the respective myotome (FIGS. 8A/8B). In one embodiment, the baseline onset current level is shown as a particular color LED in the bar graph for each myotome location and the increased onset current level value is shown as a different color LED on the bar graph. When the onset current level decreases for a nerve this may indicate that a nerve has been aided by the procedure. The decreased onset current level may also be displayed on the bar graft for the respective myotome. In a preferred embodiment, the decreased onset current level value is shown as a third color LED on the bar graph. When the onset current level remains constant, only the first color for the baseline onset current level is shown on the bar graph. In one embodiment, a blue LED is depicted for the baseline onset current level, an orange LED is depicted for an increased (over the baseline) onset current level, and a green LED is depicted for a decreased onset current level. In one embodiment when the maximum current level in the staircase does not elicit an onset EMG response for a myotome, the baseline LED may be set to flash to indicate this condition. Accordingly, a clinician may periodically request nerve status (midline stimulation) readings to determine what impact, positive, negative, or neutral, a procedure has had on a patient. The clinician can make this assessment by viewing the bar graphs on the display shown in FIG. 8 for each of the myotome locations.

The above determined initial set baseline neuro-muscular response onset current levels for each nerve pathway (myotome location) may then be used in the first (i.e.: nerve sensing) aspect of the present invention, in which a system is provided for detecting the presence of a spinal nerve adjacent to the distal end of a single probe 20, or either of probes 20 or 22. (It is to be understood, however, that the forgoing nerve status system (which may experimentally determine neuro-muscular response onset values) is an optional aspect of the present nerve detection system. As such, it is not necessary to determine such relative or absolute neuro-muscular response baseline onset current levels as set forth above prior to nerve detection. Rather, generally expected or previously known current onset levels may instead be used instead. Such generally expected or previously known current onset levels may have been determined by experiments performed previously on other patients.

In accordance with the first aspect of the present invention, nerve detection (performed as the surgical tool or probe is advancing toward the operative site), or nerve surveillance (performed in an ongoing fashion when the surgical tool or probe is stationary has already reached the operative site) may be carried out, as follows.

The first (nerve detection/surveillance) aspect of the invention will now be set forth.

Returning to FIG. 1, a system is provided to determine whether a nerve is positioned closely adjacent to either of two probes 20 and 22. In accordance with the present invention, probes 20 and 22 can be any manner of surgical tool, including (electrified) cannulae through which other surgical tools are introduced into the patient. In one aspect of the invention only one probe (e.g.: probe 20) is used. In another aspect, as illustrated, two probes (e.g.: 20 and 22) are used. Keeping within the scope of the present invention, more than two probes may also be used. In one preferred aspect, probe 20 is an electrified cannula and probe 22 is a "confirmation electrode" which can be inserted through cannula/probe 20, as will be explained. Probes 20 and 22 may have electrified distal ends, with electrodes 21 and 23 positioned thereon, respectively. (In the case of probe 20 being a cannula, electrode 21 may be positioned on an electrified distal end of the cannula, or alternatively, the entire surface of the electrified cannula may function as the electrode).

Nerve detection is accomplished as follows. A stimulus pulse is passed between electrode 21 (disposed on the distal end of a probe 20) and patient return electrode 30. In instances where a second probe (22) is also used, a stimulus pulse is passed between electrode 23 (disposed on the distal end of a probe 22) and patient return electrode 30. In one aspect, electrodes 21 or 23 operate as cathodes and patient return electrode 30 is an anode. In this case, probes 20 and 22 are monopolar. Preferably, when simultaneously using two probes (20 and 22) the stimulus pulse emitted by each of electrodes 21 and 23 is multiplexed, so as to distinguish between their signals.

It should be understood that electrodes 21 and 23 could be replaced by any combination of multiple electrodes, operating either in monopolar or bipolar mode. In the case where a single probe has multiple electrodes (replacing a single electrode such as electrode 21) probe 20 could instead be bi-polar with patient return electrode 30 no longer being required.

Subsequent to the emission of a stimulus pulse from either of electrodes 21 or 23, each of myotome locations ML1 through MR3 are monitored to determine if they exhibit an EMG response.

Figure 3:
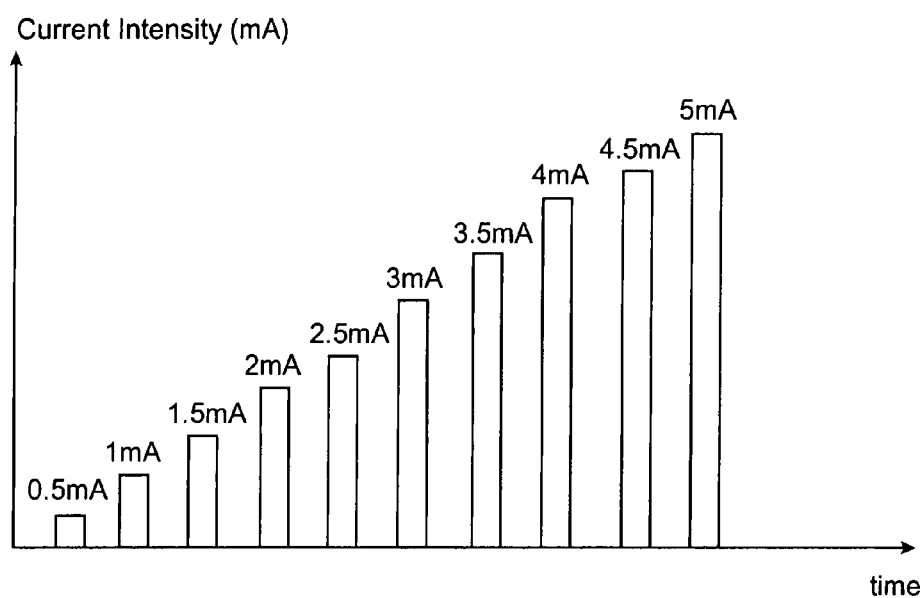
FIG. 3 shows a current intensity staircase for an electromyographic stimulation pulse for a nerve detection electrode disposed on a probe.

In a preferred aspect, as shown in FIG. 3, the intensity of the stimulus pulse passing between electrodes 21 and 30 or between 22 and 30 is preferably varied over time. Most preferably, the current intensity level of the stimulus pulse is incrementally increased step-by-step in a "staircase" fashion. As can be seen, the current may be increased in ten 0.5 mA steps from 0.5 mA to 5.0 mA. This stimulus pulse is preferably increased one step at a time until a neuro-muscular (i.e., EMG) response to the stimulus pulse is detected in each of myotome locations ML1 through MR3.

For myotome locations that exhibit an EMG response as a result of the stimulus pulse, the present invention then records the lowest amplitude of current required to elicit such a response. Subsequently, this stimulus level is interpreted so as to produce an appropriate warning indication to the user that the surgical tool/probe is in close proximity to the nerve.

For example, in a simplified preferred aspect, the staircase of stimulus pulses may comprise only three levels, (rather than the 8 levels which are illustrated in FIG. 3). If an EMG response is recorded at a particular myotome location for only the highest level of stimulation (i.e.: the third step on a 3-step staircase), then the system could indicate a "low" alarm condition (since it took a relatively high level of stimulation to produce an EMG response, it is therefore unlikely that the tool/probe distal tip(s) are in close proximity to a nerve). If an EMG response is instead first recorded when the middle level of stimulation (i.e.: the second step on the 3-step staircase) is reached, then the system could indicate a "medium" alarm condition. Similarly, if an EMG response is recorded when the lowest level of stimulation (i.e.: the first step on the 3-step staircase) is reached, then it is likely that the probe tips(s) are positioned very close to a nerve, and the system, could indicate a "high" alarm condition.

As can be appreciated, an important advantage of increasing the stimulus current intensity in a "staircase" function, increasing from lower to higher levels of current intensity is that a "high" alarm condition would be reached prior to a "low" alarm condition being reached, providing an early warning to the surgeon. Moreover, as soon as a "high" alarm condition is reached, the present invention need not continue through to the end (third step) of the staircase function. In preferred aspects, when the current level of the applied signal to the probe (20 or 22) elicits an EMG response greater than the pre-determined onset EMG response, the current level is not increased.

In the above-described simplified (only three levels of stimulation) illustration of the invention, it was assumed that all nerves respond similarly to similar levels of stimulation, and the proximity (nerve detection) warning was based upon this assumption. Specifically, in the above-described simplified (three levels of stimulation) illustration, there was an assumed one-to-one (i.e. linear) mapping of the EMG onset value data onto the response data when determining what level of proximity warning indication should be elicited, if any. However, in the case of actual spinal nerve roots, there is not only a natural variability in response onset value threshold, but there is often a substantial variation in neuro-muscular response onset values between the nerve pathways caused as a result of certain disease states, such as nerve root compression resulting from a herniated intervertebral disc.

Accordingly, in a preferred aspect of the present invention, the initial "baseline" neuro-muscular EMG response onset value data set which characterizes the relative EMG onset values of the various nerve roots of interest, (as described above), is used to guide the interpretation of EMG response data and any subsequent proximity warning indication, as follows.

Referring back to FIG. 1 and Table 1, the stimulation staircase transmitted between electrodes 11 and 13 (or 12 and 14) resulted in measures neuro-muscular (i.e.: EMG) response onset values of 4, 16, 20, 16, 24 and 12 mA at myotome locations ML1, ML2, ML3, MR1, MR2 and MR3, respectively. As can be seen, twice the intensity of current was required to produce a neuro-muscular response at MR2 as was required to produce a neuro-muscular response at MR3 (since "24" mA is twice as big as "12" mA). Thus, the nerve pathway to MR3 is more "sensitive" than to MR2 (since MR3 is able to exhibit a neuro-muscular response at ½ of the current intensity required to exhibit a neuro-muscular response at MR2). Consequently, during nerve detection, when electrode 21 or 23 (positioned on the distal end of tool/probe 20 or 22) is positioned adjacent the nerve root affiliated with MR3, twice the current stimulation intensity was required to produce an EMG response. In contrast, when electrode 21 or 23 (on the distal end of tool/probe 20 or 22) was positioned adjacent to the nerve root affiliated with MR2, the same level of stimulation that produced a response at MR3 would not produce a response at MR2.

In accordance with preferred aspects of the present invention, the sensitivities of the various spinal nerve pathways (to their associated myotomes) are incorporated into the nerve detection function of the invention by incorporating the various neuro-muscular response onset values, as follows.

A decision is made that either of electrodes 21 or 23 are positioned adjacent to a spinal nerve when a neuro-muscular response is detected at a particular myotome location at a current intensity level that is less than, (or optionally equal to), the previously measured or input EMG response onset value for the particular spinal nerve corresponding to that myotome. For example, referring to myotome location ML1, the previously determined neuro-muscular response onset level was 4 mA, as shown in Table 1. Should a neuro-muscular response to the stimulus pulse be detected at a current intensity level at or below 4 mA, this would signal the operator that the respective probe electrode 21 (or 23) emitting the stimulus pulse is in close proximity to the spinal nerve. Similarly, the neuro-muscular response onset value for myotome location ML2 was determined to be 16 mA, as shown in Table 1. Accordingly, should a neuro-muscular response be detected at a current intensity level of less than or equal to 16 mA, this would indicate that respective probe electrode 21 (or 23) emitting the stimulus pulse is in close proximity to the spinal nerve.

Figure 4:
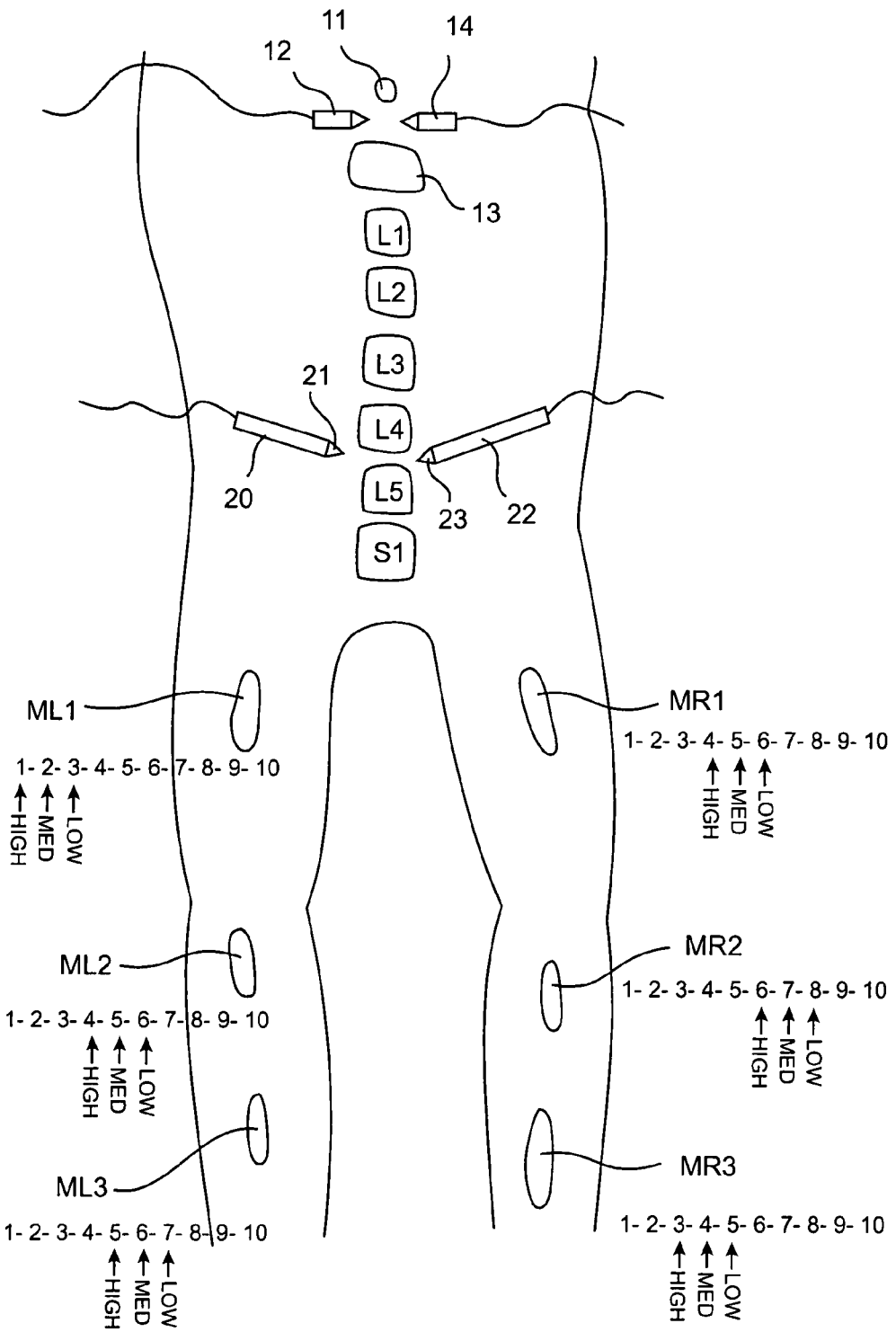
FIG. 4 corresponds to FIG. 1, but also shows exemplary "high", "medium" and "low" warning levels corresponding to exemplary neuro-muscular response onset levels.

In addition, as illustrated in FIG. 4, "high", "medium" and "low" warning levels may preferably be mapped onto each stimulation staircase level for each myotome location. For example, the neuro-muscular onset level for ML1 was 4 mA, corresponding to the first level of the 8-level status electrode current staircase of FIG. 2. Thus, the first (4 mA) step on the staircase is assigned a "high" warning level. Level two (8 mA) is assigned a "medium" warning level and level three (12 mA) is assigned a "low" warning level. Thus, if an EMG response is recorded at ML1 at the first stimulation level, (4 mA), a "high" proximity warning is given. If a response is detected at the second level (8 mA), then a "medium" proximity warning is given. If a response is detected at the third level (12 mA), then a "low" proximity warning is given. If responses are detected only above the third level, or if no responses are detected, than no warning indication is given.

Similarly, for ML2, with a onset value of 16 mA, (i.e.: the fourth level in the status electrode current staircase sequence), the "high", "medium" and "low" warning levels are assigned starting at the fourth step on the status electrode current staircase, with the fourth step being "high", the fifth level being "medium" and the sixth level being "low", respectively, as shown. Accordingly, if an EMG response is detected for ML2 at (or above) the first, second, third, or fourth surveillance levels, (i.e.: 4, 18, 12 or 16 mA), then a "high" warning indication will be given. For a response initially detected at the fifth level (i.e.: 20 mA), then a "medium" warning indication is given. If a response is not detected until the sixth level (i.e.: 24 mA), then a "low" warning indication is given. If responses are detected only above the sixth level, or not at all, then no indication is given. Preferably, each of myotome locations ML1 through MR3 are monitored at conditions indicating "high", "medium" and "low" likelihood of a nerve being disposed adjacent the surgical tool/probe.

As can be seen in FIG. 4, ten levels are shown for each of the myotome locations, whereas the illustrated status electrode current staircase has only eight levels. These optional levels "9" and "10" are useful as follows. Should scaled level 8 be the minimum onset level at which a neuro-muscular response is detected, levels "9" and "10" can be used to indicate "medium" and "low" warning levels, respectively.

As explained above, the various neuro-muscular response current onset levels used in detection of spinal nerves may either have been either determined in accordance with the second aspect of the present invention, or may simply correspond to a set of known or expected values input by the user, or pre-set into the system's hardware/software. In either case, an advantage of the present system is that different neuro-muscular response onset value levels may be used when simultaneously sensing for different nerves. An advantage of this is that the present invention is able to compensate for different sensitivities among the various spinal nerves.

As can be seen comparing the current intensities of stimulus electrodes 11 and 13 (or 12 and 14) as shown in FIG. 2 (i.e.: up to 32 mA) to the current intensities of probe electrodes 21 and 23 as shown in FIG. 3 (i.e.: up to 5.0 mA), the current intensities emitted by probe electrodes 21 and 23 are less than that of electrodes 12 and 14. This feature of the present invention is very advantageous in that electrodes 21 and 23 are positioned much closer to the spinal nerves. As such, electrodes 21 and 23 do not depolarize a large portion of the cauda equina, as do electrodes 12 and 14. In addition, the placement of electrode 11 in the epidural space ensures that the electrode is at a relatively known distance from the spinal nerves.

In an optional preferred aspect of the invention, if a neuro-muscular response (greater than the onset EMG response) is detected for all six myotome sensing locations ML1 through MR3 before all of the steps on the staircase is completed, the remaining steps need not be executed.

Moreover, if it has been determined that a maximal level of stimulation is required to elicit an EMG response at a particular myotome sensing location, then only the top three stimulation levels need to be monitored during the neuro-muscular response detection sequence. In this case, the top three monitored levels will correspond to "high", "medium", and "low" probabilities of the surgical tool/probe being disposed adjacent the a nerve. In another optional aspect, if any of the myotome locations do not respond to the maximum stimulation level (i.e.: top step on the staircase), they are assigned the maximum scale value (i.e.: a "low" warning indication).

Figure 5:
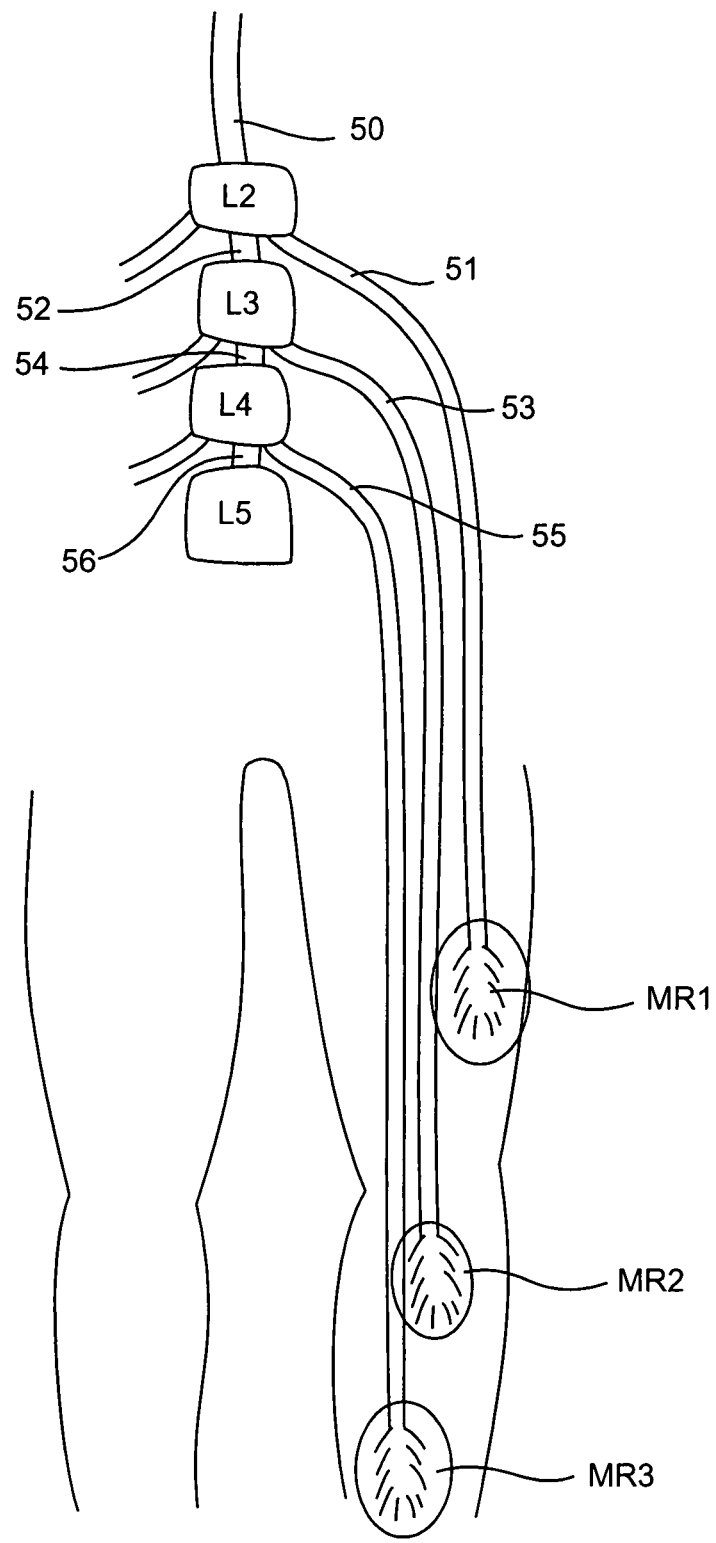
FIG. 5 shows a patient's spinal nerves, and corresponding myotome monitoring locations.

Preferably, each of the spinal nerves monitored at myotome locations ML1 through MR3 will correspond to nerves exiting from successive vertebrae along the spine. For example, as shown in FIG. 5, a main spinal nerve 50 will continuously branch out downwardly along the spinal column with spinal nerve 51 exiting between vertebrae L2 and L3 while nerve 52 passes downwardly. Spinal nerve 53 exits between vertebrae L3 and L4 while spinal nerve 54 passes downwardly to L4. Lastly, spinal nerve 55 will exit between vertebrae L4 and L5 while spinal nerve 56 passes downwardly. As can be seen, neuro-muscular (i.e., EMG) response measurements taken at myotome location MR1 will correspond to EMG signals in spinal nerve 51, response measurements taken at myotome location MR2 correspond to EMG signals in spinal nerve 53, and response measurements taken at myotome location MR3 correspond to EMG signals in spinal nerve 55.

In accordance with the present invention, the detection of a neuro-muscular (EMG) response, whether in accordance with the first (i.e.: nerve detection), or second (i.e.: establishing initial "baseline" neuro-muscular response onset values) aspect of the invention, may be accomplished as follows.

Figure 6:
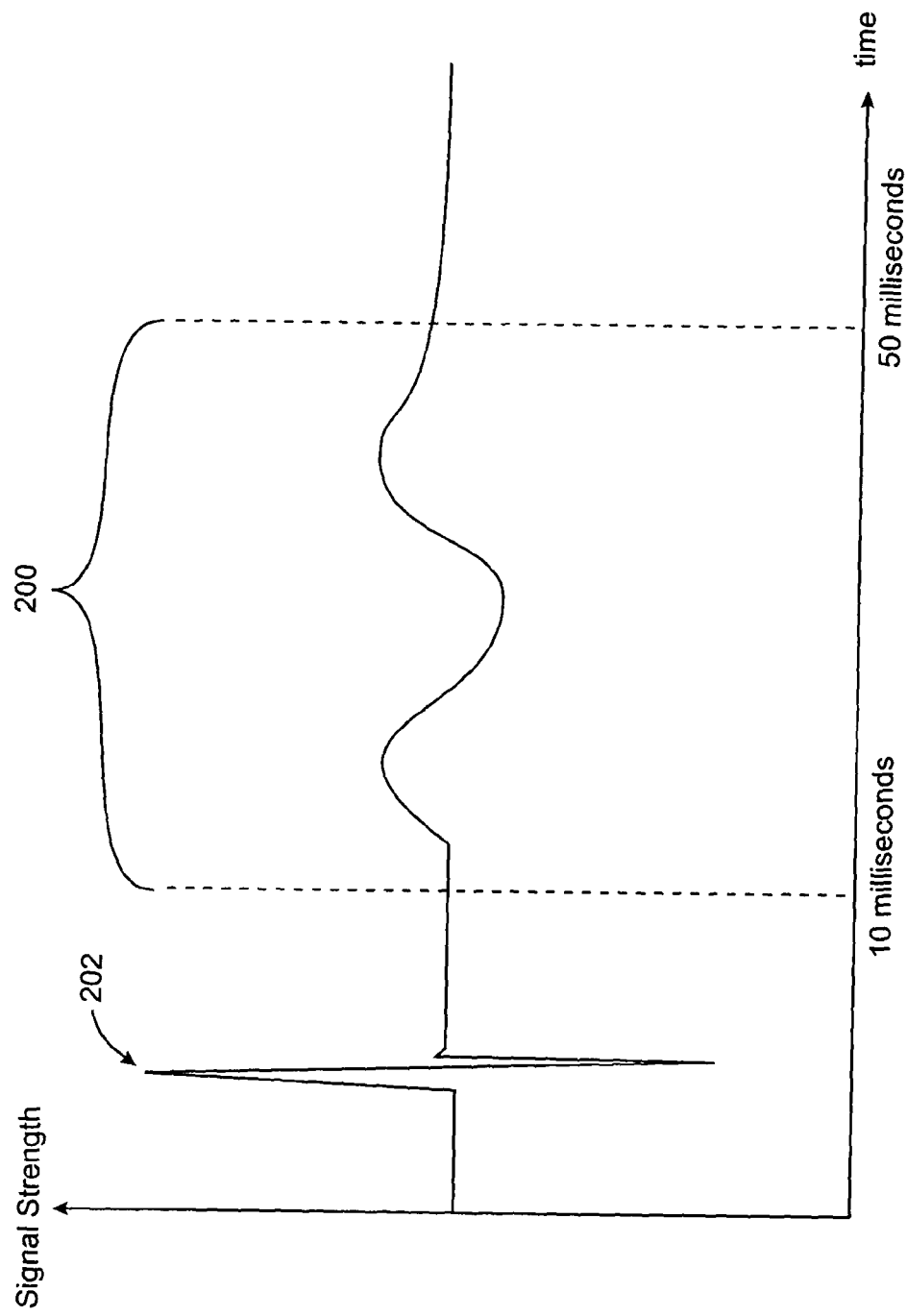
FIG. 6 is an illustration of the waveform characteristics of a stimulus pulse and a corresponding neuro-muscular (EMG) response as detected at a myotome location.
Figure 7:
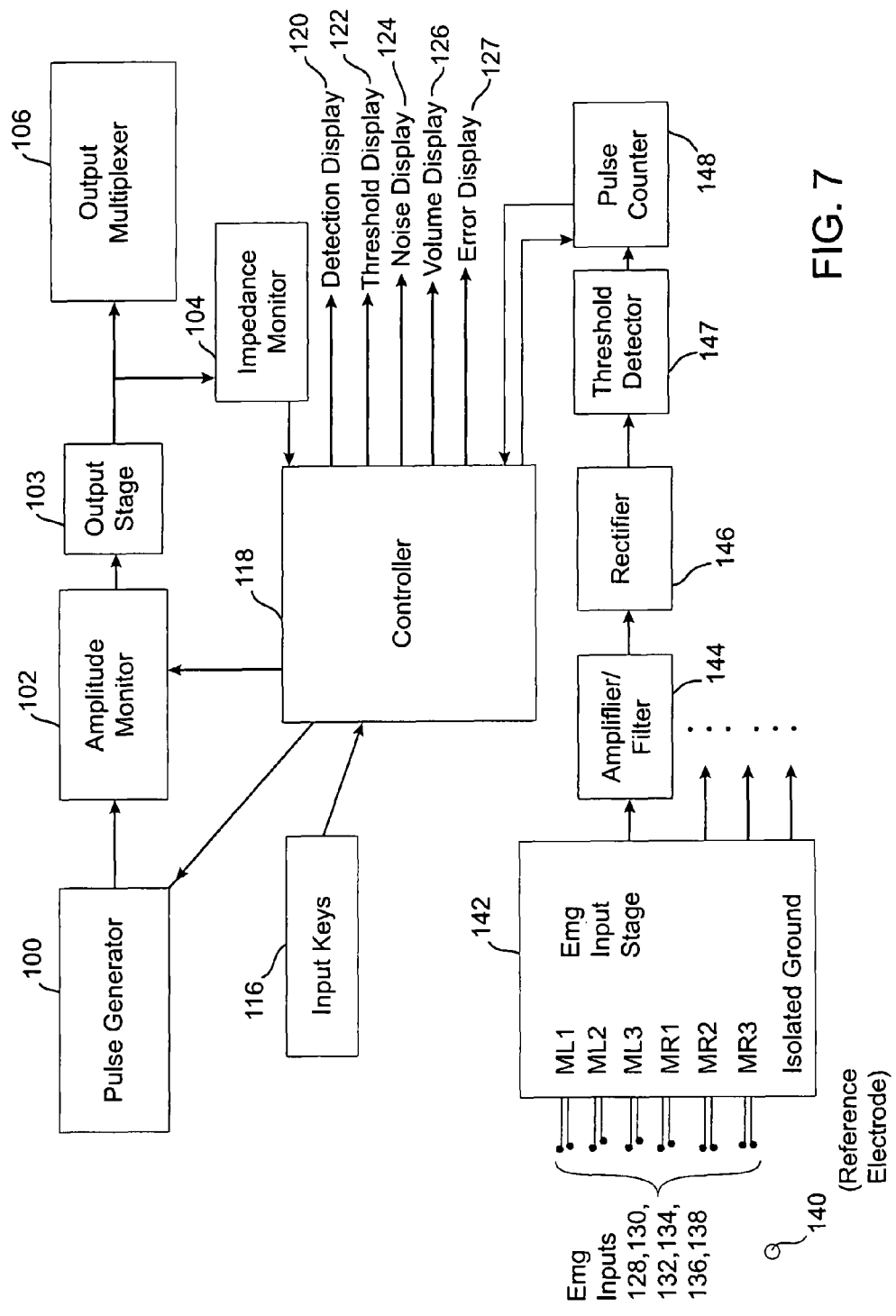
FIG. 7 is a schematic diagram of a nerve detection system.

Referring to FIG. 6, an illustration of the waveform characteristics of a stimulus pulse and a corresponding neuro-muscular (EMG) response as detected at a myotome location is shown. An "EMG sampling window" 200 may be defined at a fixed internal of time after the stimulus pulse 202 is emitted. The boundaries of window 200 may be determined by the earliest and latest times that an EMG response may occur relative to stimulus pulse 202. In the case of stimulation near the lumbar spine, these times are, for example, about 10 milliseconds and 50 milliseconds, respectively.

During EMG sampling window 101, the EMG signal may optionally be amplified and filtered in accordance with guidelines known to those skilled in the art. The signal may then be rectified and passed through a threshold detector to produce a train of pulses representing the number of "humps" of certain amplitudes contained in the EMG waveform. A re-settable counting circuit may then count the number of humps and a comparator may determine whether the number of pulses is within an acceptable range. By way of example only, the number of acceptable pulses for EMG responses elicited by stimulation in the lumbar spine region may range from about two to about five. If only one pulse is counted, then it is unlikely that a true EMG response has occurred, since true EMG waveforms are typically biphasic (having at least one positive curved pulse response and one negative curved pulse response) resulting in at least two pulses. This pulse-counting scheme helps to discriminate between true EMG waveforms and noise, since noise signals are typically either sporadic and monophasic (and therefore produce only one pulse) or repetitive (producing a high number of pulses during the EMG sampling window).

In a further optional refinement, a separate noise-sampling window may be established to remove noise present in the EMG responses to increase the ability of the system to discriminate between true EMG responses and false responses caused by noise. The boundaries of noise sampling window are chosen such that there is no significant change of a true EMG signal occurring during the window. For example, it may be deemed acceptable that one curved pulse of an EMG response may be comprised primarily of noise, but if more than one curved pulse of an EMG response is primarily comprised of noise, an alarm would be triggered indicating that excess noise is present on that particular channel.

In preferred aspects of the present invention, both the optional second aspect of determining the neuro-muscular response onset values for each of the plurality of spinal nerves and the first aspect of sensing to detect if a nerve is positioned adjacent to a surgical tool/probe are repeated over time. Preferably, the sensing of whether a nerve is positioned adjacent to a surgical tool/probe is continuously repeated in very short intervals of time, such that the operator can be warned in real time as the surgical tool/probe is advanced toward the nerve. The present system of determining the neuro-muscular response onset values for each of the plurality of spinal nerves is also preferably repeated, and may be repeated automatically, or under operator control.

Typically, the above two aspects of the present invention will not be carried out simultaneously. Rather, when the neuro-muscular response onset values are being determined (using electrodes 11 and 13 or 12 and 14), the operation of probe electrodes 21 and 23 will be suspended. Conversely, when sensing to determine whether a nerve is positioned adjacent either of probes 20 or 22, the operation of stimulation electrodes 11 and 13 or 12 and 14 will be suspended. A standard reference electrode 32 may be used for grounding the recording electrodes at the myotomes.

FIG. 6 depicts a particular exemplary embodiment of the present invention. Other embodiments are also possible, and are encompassed by the present invention. Pulse generator 100 creates pulse trains of an appropriate frequency and duration when instructed to do so by controller 118. By way of example, the pulse frequency may be between 1 pulse-per-second and 10 pulses-per-second, and the pulse duration may be between 20 µsec and 300 µsec. Pulse generator 100 may be implemented using an integrated circuit (IC), such as an ICL75556 (Intensity) or generated by a software module. Amplitude modulator 102 produces a pulse of appropriate amplitude as instructed by controller 118, and may comprise a digital-to-analog converter such as a DAC08 (National Semiconductor). The output of amplitude modulator 102 drives output stage 103, which puts out a pulse of the desired amplitude. Output stage 103 may comprise a transformer coupled, constant-current output circuit. The output of output stage 103 is directed through output multiplexer 106 by controller 118 to the appropriate electrodes, either to status (baseline) electrodes 11 and 13, or to a combination of screw test probe 109, probe electrode 21, 23 and patient return electrode 13. Impedance monitor 104 senses the voltage and current characteristics of the output pulses and controller 118 elicits an error indication on error display 127 if the impedance falls above or below certain pre-set limits. Input keys 116 may be present on a front panel of a control unit of the present invention, as depicted in FIG. 8, to allow the user to shift between modes of operation.

EMG inputs 128 to 138 comprise the six pairs of electrodes used to detect EMG activity at six different myotome locations. It will be appreciated that the number of channels may vary depending upon the number of nerve roots and affiliated myotomes that need to be monitored. A reference electrode 140 may also be attached to the patient at a location roughly central to the groupings of EMG electrodes 128 to 138 to serve as a ground reference for the EMG input signals. Electrodes 128 to 140 may either be of the needle-type or of the gelled foam type, or of any type appropriate for detecting low-level physiological signals. EMG input stage 142 may contain input protection circuit comprising, for example, gas discharge elements (to suppress high voltage transients) and/or clamping diodes. Such clamping diodes are preferably of the low-leakage types, such as SST-pads (Siliconix). The signal is then passed through amplifier/filter 144, which may amplify the signal differentially using an instrumentation amplifier such as an AD620 (Analog Devices). The overall gain may be on the order of about 10,000:1 to about 1,000,000:1, and the low and high filter bands may be in the range of about 1-100 Hz and 500 to 5,000 Hz, respectively. Such filtering may be accomplished digitally, in software, or with discrete components using techniques well known to those skilled in the art. The amplified and filtered signal then passes through rectifier 141, which may be either a software rectifier or a hardware rectifier. The output of rectifier 146 goes to threshold detector 147 which may be implemented either in electronic hardware or in software. The output of threshold detector 147 then goes to counter 148 which may also be implemented by either software or hardware.

Controller 118 may be a microcomputer or microcontroller, or it may be a programmable gate array, or other hardware logic device. Display elements 120 to 127 may be of any appropriate type, either individually implemented (such as with multicolor LEDs) or as an integrated display (such as an LCD).

What is claimed is:

1. A method for testing the structural integrity of a spinal pedicle of a patient through a minimally invasive operative corridor to detect a defect in the structural integrity of a pedicle wall surrounding a pedicle screw path formed through the pedicle, said method comprising:
   (a) advancing an elongate element to said pedicle via a minimally invasive approach through said patient;
   (b) advancing a stimulation element through said elongate element to said pedicle, said stimulation element communicatively linked to a controller that directs application of an electrical stimulus;
   (c) applying an electrical stimulus to said pedicle via said stimulation element;
   (d) electrically monitoring with a sensor communicatively linked to said controller a muscle myotome associated with a spinal nerve lying adjacent to said pedicle to detect if an onset neuro-muscular response occurs in response to the application of said electrical stimulus;
   (e) said controller automatically adjusting the magnitude of the electrical stimulus until said onset neuro-muscular response is detected, said controller determining the electrical stimulus magnitude that caused said onset neuro-muscular response;
   (f) said controller interpreting the electrical stimulus magnitude which caused said onset neuro-muscular response and outputting an indicator indicative of the structural integrity of the pedicle; and
   (g) redirecting the pedicle screw path when a defect in the structural integrity of the pedicle wall is indicated.

2. The method of claim 1, wherein said stimulation element comprises at least one of a probe and a surgical tool, and step (c) involves applying said electrical stimulus from an electrode disposed on the distal end of said at least one of a probe and surgical tool.

3. The method of claim 1, wherein said pedicle is disposed within one of the cervical, thoracic, and lumbar region of the patient's spine.

4. The method of claim 1, wherein said onset neuro-muscular response is an electromyography response from a muscle coupled to said spinal nerve.

5. The method of claim 1, wherein the sensor of step (d) is an EMG electrode electrically coupled to said muscle myotome.

6. The method of claim 1, wherein the indicator of step (f) is a visual indicator.

7. The method of claim 1 and further, wherein the indicator of step (f) is an audible indicator.

8. The method of claim 1, wherein step (c) involves applying said electrical stimulus to a proximal end of a pedicle screw inserted into said pedicle along said pedicle screw path.

9. The method of claim 1, wherein said elongate element comprises a cannula.

10. The method of claim 1, wherein the electrical stimulus comprises a plurality of current pulses.

11. The method of claim 10, wherein the plurality of current pulses are automatically increased in constant increments over time until said onset neuromuscular response is determined.

12. The method of claim 10, wherein the plurality of electrical stimulus pulses are increased incrementally within a range including a minimum stimulation current level and a maximum stimulation current intensity.

13. A method for performing pedicle integrity assessments with minimal tissue disruption to detect a defect in the structural integrity of a pedicle wall surrounding a pedicle screw path formed through the pedicle, said method comprising:
   (a) advancing a minimally invasive cannula via a minimally invasive approach to a pedicle target site within a patient;
   (b) delivering a stimulation signal to said pedicle target site via a stimulation element disposed through said cannula, said stimulation element communicatively linked to a controller that directs application of the electrical stimulus; and
   (c) electrically monitoring with a sensor communicatively linked to said controller a muscle myotome innervated by a nerve adjacent to said pedicle to detect when an onset neuro-muscular response occurs in a muscle myotome innervated by said nerve in response to the delivery of said stimulation signal and determine the intensity level of the electrical stimulus that causes said onset neuro-muscular response;
   (d) said controller interpreting the determined intensity level of the electrical stimulus that caused said onset neuro-muscular response and outputting at least one of visual and audible indicia indicative of the structural integrity of the pedicle; and
   (e) redirecting the pedicle screw path when a defect in the structural integrity of the pedicle wall is indicated.

14. The method of claim 13, wherein step (b) comprises automatically increasing the intensity level of the stimulation signal until said onset neuro-muscular response is detected.

15. The method of claim 14, wherein step (b) further comprises delivering said stimulation signal as a plurality of electrical stimulus pulses that increase over time.

16. The method of claim 15, wherein the plurality of electrical stimulus pulses comprises current pulses varied incrementally within a range including a minimum stimulation current intensity and a maximum stimulation current intensity.

17. The method of claim 13, wherein said onset neuro-muscular response is an electromyography response from a muscle coupled to said nerves.

18. The method of claim 17, wherein said sensor is an EMG electrode electrically coupled to said muscle myotome.

19. The method of claim 13, wherein said pedicle target site is a proximal end of a pedicle screw implanted in said pedicle along said pedicle screw path.

20. The method of claim 13, wherein said pedicle is within one of the cervical, thoracic, and lumbar regions of the patient's spine.

21. The method of claim 13, wherein said stimulation element comprises at least one of a probe and a surgical tool, and step (b) involves delivering said stimulation signal from an electrode disposed on the distal end of said at least one of a probe and surgical tool.

22. The method of claim 13, wherein step (d) involves visually indicating an intensity level of the stimulus that evoked the onset neuro-muscular response for said nerve and illuminating lights which correspond to predetermined warnings.

23. The method of claim 13, wherein step (d) involves sounding an alarm if said determined intensity level is less than a predetermined intensity level.

* * * * *